United States Patent [19]

Hagen et al.

[11] Patent Number: 5,130,434
[45] Date of Patent: Jul. 14, 1992

[54] PREPARATION OF 3-METHYLQUINOLINE-8-CARBOXYLIC ACID

[75] Inventors: Helmut Hagen, Frankenthal; Jacques Dupuis, Ludwigshafen; Karlheinz Arbogast, Mutterstadt, all of Fed. Rep. of Germany

[73] Assignee: BASF Aktiengesellschaft, Ludwigshafen, Fed. Rep. of Germany

[21] Appl. No.: 571,232

[22] Filed: Aug. 23, 1990

[30] Foreign Application Priority Data

Sep. 9, 1989 [DE] Fed. Rep. of Germany ....... 3930167

[51] Int. Cl.$^5$ .................................... C07D 215/48
[52] U.S. Cl. .................................... 546/170
[58] Field of Search .................................... 546/170

[56] References Cited

U.S. PATENT DOCUMENTS

| 4,715,889 | 12/1987 | Hagen et al. | 546/168 |
| 4,845,226 | 6/1989 | Hagen et al. | 546/170 |
| 5,006,659 | 4/1991 | Hagen et al. | 546/170 |

FOREIGN PATENT DOCUMENTS 0282778  9/1988  European Pat. Off. .
0294685 12/1988  European Pat. Off. .

*Primary Examiner*—Patricia L. Morris
*Assistant Examiner*—Lenora Miltenberger
*Attorney, Agent, or Firm*—Keil & Weinkauf

[57] ABSTRACT

3-Methylquinoline-8-carboxylic acid I

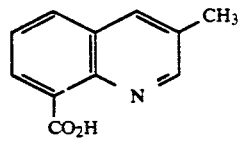

and derivatives thereof are prepared by reacting o-toluidine II or a derivative thereof

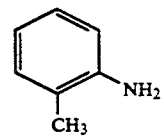

with methacrolein II

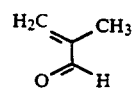

in 70–90% strength by weight sulfuric acid in the presence of iodine or of an iodine compound, and oxidizing the resulting 3,8-dimethylquinoline IV or a derivative thereof

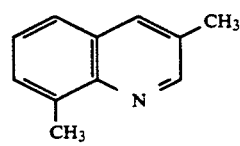

with nitric acid in a solution containing sulfuric acid, in the presence of vanadium ions, by a process in which, in the sulfuric acid-containing reaction solution of the 3,8-dimethylquinoline IV, the byproducts of the reaction are first decomposed by oxidation, the resulting 3,8-dimethylquinoline solution is concentrated by distillation and the 3,8-dimethylquinoline is then oxidized in situ with nitric acid to give the 3-methylquinoline-carboxylic acid.

4 Claims, No Drawings

PREPARATION OF 3-METHYLQUINOLINE-8-CARBOXYLIC ACID

The present invention relates to a novel process for the preparation of 3-methylquinoline-8-carboxylic acid I

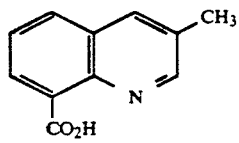

or a derivative thereof by reacting o-toluidine II or a derivative thereof

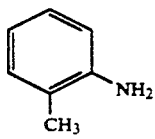

with methacrolein III

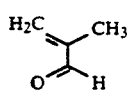

in 70–90% strength by weight sulfuric acid in the presence of iodine or of an iodine compound, and oxidizing the resulting 3,8-dimethylquinoline IV or a derivative thereof

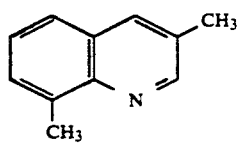

With nitric acid in a solution containing sulfuric acid, in the presence of vanadium ions to give 3-methylquinoline-8-carboxylic acid.

EP-A 294 685 describes the synthesis of 3,8-dimethylquinoline from o-toluidine and methacrolein in the presence of iodine in a solution containing sulfuric acid.

EP-A 282 778 discloses the oxidation of 3,8-dimethylquinoline and derivatives thereof to 3-methylquinoline-8-carboxylic acid and derivatives thereof by means of nitric acid in the presence of vanadium ions in a solution containing sulfuric acid. However, it is expressly pointed out that the purity of the educts is critical for obtaining an advantageous result in this reaction.

However, the prior art synthesis of 3-methylquinoline-8-carboxylic acid I and its derivatives is technically unsatisfactory since it requires the expensive purification of the intermediate IV. If this purification is omitted and the reaction mixture from the synthesis of IV is used directly in the oxidation stage, the yield of I decreases. In addition, the oxidation in this case is accompanied by vigorous foaming, which makes the reaction considerably more difficult in terms of process technology.

The present invention is based on the observation that the byproducts formed in the first reaction stage in the synthesis of IV are responsible both for the lower yields of I and for the foam formation in the oxidation of IV to I.

We have found that these byproducts are mainly polymethacrylates, which are formed under the reaction conditions of the fusion of II with III. When 1.4 moles of III are used per mole of II, the amount of these byproducts is about 5–10% by weight, based on the 3,8-dimethylquinoline IV.

It is an object of the present invention to provide a one-stage process for the preparation of 3-methylquinoline-8-carboxylic acid.

We have found that this object is achieved by a process for the preparation of 3-methylquinoline-8-carboxylic acid I

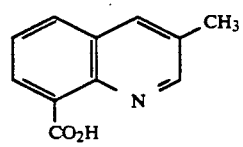

or a derivative thereof by reacting o-toluidine II or a derivative thereof

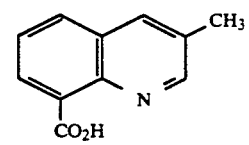

With methacrolein III

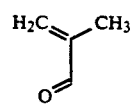

or a derivative thereof in 70–90% strength by weight sulfuric acid in the presence of iodine or of an iodine compound, and oxidizing the resulting 3,8-dimethylquinoline IV or a derivative thereof

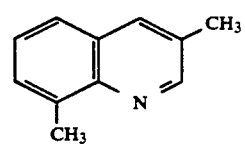

with nitric acid in a solution containing sulfuric acid, in the presence of vanadium ions, wherein, in the sulfuric acid-containing reaction solution of the 3,8-dimethylquinoline IV, the byproducts of the reaction are first decomposed by oxidation, the resulting 3,8-dimethylquinoline solution is concentrated by distillation and the 3,8-dimethylquinoline is then oxidized in situ with nitric acid to give 3-methylquinolinecarboxylic acid.

The core of the novel process is based on the fact that the sulfuric acid-containing reaction solution is freed from byproducts by oxidation, so that isolation of the 3,8-dimethylquinoline is unnecessary. Consequently, both fusion and oxidation can take place in succession in one medium (in situ).

From 5 to 65% strength by weight aqueous nitric acid is a particularly suitable oxidizing agent for the oxidative decomposition of the byproducts of the fusion.

For the oxidative decomposition of the byproduct of the reaction, nitric acid is added in amounts of from 1.2 to 3.0, preferably from 1.3 to 2, moles, based on compound II.

This oxidation begins at about 50° C. and takes place at a sufficient rate at from about 70° C. If the mixture is heated to above about 150° C, foam formation begins. The optimum temperature range is from 70° to 130° C. If the reaction mixture is heated so slowly that the byproducts are already partially decomposed before the maximum temperature is reached, this oxidation can also be carried out at higher temperatures.

After decomposition of the byproducts of the reaction, the sulfuric acid-containing solution of 3,8-dimethylquinoline is concentrated by distilling off excess water and is oxidized in a known manner, without further pretreatment, by adding additional nitric acid.

The novel process is suitable for the preparation of 3-methylquinoline-8-carboxylic acid and substituted 3-methylquinoline-8-carboxylic acids from the corresponding o-toluidines, in particular those of the general formula II

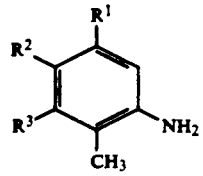

where $R^1$ to $R^3$ are each hydrogen, halogen, organic carbon-containing radicals and/or nitro groups; observations to date have shown that the nature of the substituents has only a slight effect on the process if they are inert under the reaction conditions.

Preferred radicals $R^1$ to $R^3$ in addition to hydrogen are the following groups:
halogen, such as fluorine, chlorine, bromine or iodine, in particular chlorine, methyl and aryl, in particular phenyl.

These radicals may in turn be interrupted by heteroatoms, such as nitrogen, oxygen and sulfur, or may carry further inert radicals, such as halogen, nitro, sulfonyl, arylsulfonyl and carboxyl.

The 3-methylquinoline-8-carboxylic acid I and derivatives thereof, which are more readily obtainable by the novel process, are used, for example, as crop protection agents.

EXAMPLES

General examples of the process for the preparation of 3-methylquinoline-8-carboxylic acids from o-toluidines IIa and methacrolein III Variant 1:
a) Fusion
1 mole of o-toluidine derivative was reacted with 1.4 moles of methacrolein according to Example 5 of EP-A 294685.

b) Destruction of the byproducts
140 g of 65% strength by weight nitric acid and the solution obtained from 1a were added simultaneously to a solution of 2 g (2.2 mol %) of vanadium pentoxide and 200 g of water at 90° C. in the course of 2 hours.

After the end of the addition and a further 2 hours at 90° C., the reaction mixture was heated to 155° C., 600 g of water distilling off in the course of 6 hours.

c) Oxidation to quinolinecarboxylic acid
450 g of 65% strength by weight nitric acid were then added to this concentrated reaction mixture according to Example 2 of EP-A 282778, at 155° C., while passing in 70 l/hour of air in the course of 10 hours.

Variant 2:
a) Fusion
300 ml of water were distilled off at 150° C. and 150 mbar from a reaction mixture obtained similarly to 1a from 1 mole of o-toluidine.

b) Destruction of the polymethacrylates
140 g of 65% strength by weight nitric acid and the solution obtained from 2a) were added simultaneously to a solution of 2 g (2.2 mol %) of vanadium pentoxide and 200 g of water at 90° C. in the course of 2 hours. After the end of the addition, the reaction mixture was left for a further 2 hours at 90° C. The temperature was then increased to 155° C. and 300 ml of water was distilled off in the course of 4 hours.

c) Oxidation to quinolinecarboxylic acid
The reaction mixture from 2b) was heated to 155° C. and was oxidized with 450 g of 65% strength by weight nitric acid similarly to 1c) while passing in 70 l/h of air in the course of 10 hours.

Variant 3:
a) Fusion
1 mole of o-toluidine was reacted as described under 1a).

b) Destruction of the byproducts
140 g of 65% strength by weight nitric acid and the solution obtained from 3a) were added simultaneously to 200 g of water at 90° C. in the course of 2 hours. After a further 4 hours at 90° C., the temperature was increased to 155° C., 600 g of water being distilled off in the course of 6 hours.

c) Oxidation to quinolinecarboxylic acid
2 g (2.2 mol %) of vanadium pentoxide were added to the concentrated solution of 3b). Oxidation was then carried out with 450 g of 65% strength by weight nitric acid as described under 1c), at 155° C. and while passing in 70 l/hour of air.

Variant 4:
a) Fusion
1 mole of o-toluidine was reacted similarly to 1a).

b) Destruction o the byproducts
The solution obtained from 4a) was treated as described under 1b).

c) Oxidation to quinolinecarboxylic acid
The reaction mixture treated in 4b) was oxidized with 1,000 g of 65% strength by weight nitric acid in the course of 20 hours and while passing in 70 l/h of air at 155° C., and was worked up in a conventional manner.

Variant 5:
a) Fusion
The fusion of 1 mole of o-toluidine was carried out as described under 1a).

b) Destruction of the byproducts
300 g of an oxidation solution obtained as described under, for example, 1c) and 2 g (2.2 mol %) of vanadium pentoxide were heated to 155° C. 140 g of 65% strength by weight nitric acid and the reaction mixture obtained from 5a) were added simultaneously to this solution in the course of 4 hours, 600 g of water distilling off.

c) Oxidation to quinolinecarboxylic acid

This solution from 5b), which had been simultaneously concentrated and freed from byproducts, was oxidized as described under 1c).

The details of the experiments carried out are summarized in Table 1.

After the end of the addition and a further $t_2$ hours at $T_1°$ C., the reaction mixture was heated to 155° C., $X_2$ g of water being distilled off in the course of $t_3$ hours.

c) Oxidation to 7-chloro-3-methylquinoline-8-carboxylic acid Ib

TABLE 1

| Example No. | Educt IIa $R^1$ | $R^2$ | $R^3$ | Process variant | Product Ia $R^1$ | $R^2$ | $R^3$ | Yield [%] |
|---|---|---|---|---|---|---|---|---|
| 1 | H | H | Cl | 1 | H | H | Cl | 69 |
| 2 | H | H | Cl | 2 | H | H | Cl | 69 |
| 3 | H | H | Cl | 3 | H | H | Cl | 68 |
| 4 | H | H | Cl | 5 | H | H | Cl | 67 |
| 5 | H | H | $CH_3$ | 4 | H | H | $CO_2H$ | 62 |
| 6 | H | $CH_3$ | H | 4 | H | $CO_2H$ | H | 57 |
| 7 | $CH_3$ | H | H | 1 | $CH_3$ | H | H | 62 |
| 8 | $CH_3$ | H | H | 4 | $CO_2H$ | H | H | 67 |
| 9 | H | $CH_3$ | Cl | 1 | H | $CH_3$ | Cl | 42 |
| 10 | H | $CH_3$ | Cl | 4 | H | $CO_2H$ | Cl | 35 |
| 11 | H | $CO_2H$ | Cl | 1 | H | $CO_2H$ | Cl | 28 |

The effect of the reaction parameters on the destruction of the byproducts and on the yield of the subsequent oxidation to the quinolinecarboxylic acid was investigated for the reaction of 6-chloro-o-toluidine IIb with methacrolein II to give the quinoline IVb according to the following example.

The solution concentrated under 11b) was oxidized and worked up as described under 1c).

The reaction parameters for the destruction of the byproducts and the yields of the subsequent oxidation of IVb to 7-chloro-3-methylquinoline-8-carboxylic acid Ib are shown in Table 2.

TABLE 2

| Example No. | Amount of $V_2O_5X_1$ [g] | Process variant | Temperature $T_1$ [°C.] | % by wt. of $HNO_3$ $Y_2$ [%] | Amount of HNO3 $Y_1$ [g] | Reaction time $t_1 + t_2$ [h] | Amount of water to be distilled off $X_2$ [g] | Time for dehydration $t_3$ [h] | Yield of Ib, based on IIb [%] |
|---|---|---|---|---|---|---|---|---|---|
| 1 | 2 | 1 | 90 | 65 | 140 | 4 | 600 | 6 | 69 |
| 2 | 2 | 2 | 90 | 65 | 140 | 4 | 300 | 4 | 69 |
| 3 | 0 | 3 | 90 | 65 | 140 | 6 | 600 | 6 | 68 |
| 5 | 2 | 5 | 155 | 65 | 140 | 4 | 600 | 0 | 67 |
| 12 | 2 | 12 | 50 | 65 | 140 | 14 | 600 | 7 | 65 |
| 13 | 2 | 12 | 70 | 65 | 140 | 8 | 600 | 7 | 67 |
| 14 | 2 | 12 | 90 | 5 | 1820 | 10 | 2220 | 20 | 68 |
| 15 | 2 | 12 | 90 | 30 | 304 | 6 | 704 | 7 | 69 |
| 16 | 2 | 12 | 110 | 65 | 140 | 4 | 600 | 6 | 68 |

Variant 12:

a) Fusion 1.4 moles of methacrolein III were added to 1 mole (141.5 g) of 6-chlorotoluidine IIb according to Example 5 of EP-A 294685.

b) Destruction of the byproducts $Y_1$ g of $Y_2$ % strength by weight nitric acid (1.44 moles) and the solution obtained from 11a) were added simultaneously to a solution of $X_1$ at $T_1°$ C. in the course of $t_1$ hours.

We claim:

1. A process for the preparation of 3-methylquinoline-8-carboxylic acid I

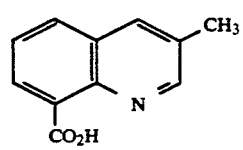

or a derivative thereof by reacting o-toluidine II or a derivative thereof

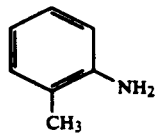  II with methacrolein III

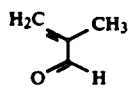  III in 70–90% strength by weight sulfuric acid in the presence of iodine or of an iodine compound to obtain a reaction mixture containing 3,8-dimethylquinoline IV or a derivative thereof

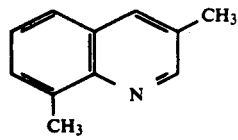  IV oxidizing said reaction mixture, without isolation of 3,8-dimethylquinoline IV or a derivative thereof, at 50° C. to 150° C. with nitric acid in a solution containing sulfuric acid, in the presence of vanadium ions, in an amount sufficient to decompose the byproducts in the reaction mixture but prevent oxidation of the 8-methyl group, to obtain a second reaction mixture, concentrating said second reaction mixture by distillation, and oxidizing the distilled second reaction mixture in situ with nitric acid in an amount sufficient to produce the 3-methylquinoline-8-carboxylic acid I.

2. A process as defined in claim 1, wherein 5 to 65% strength by weight nitric acid is used for decomposing the byproducts of the reaction.

3. A process as defined in claim 2, wherein the byproducts of the reaction are decomposed at from 70° to 130° C.

4. A process as defined in claim 2, wherein from 1.2 to 3.0 moles of nitric acid per mole of II are used for decomposing the byproducts of the reaction.

* * * * *